(12) United States Patent
Dawson et al.

(10) Patent No.: US 7,858,320 B2
(45) Date of Patent: Dec. 28, 2010

(54) METHOD, SUBSTANCES AND KITS FOR LABELING POPULATION OF RNA AND OTHER SUBSTANCES CONTAINING VICINAL DIOLS

(75) Inventors: Elliott P. Dawson, Murfreesboro, TN (US); Kristie E. Womble, Franklin, TN (US)

(73) Assignee: BioVentures, Inc., Murfreesboro, TN (US)

( * ) Notice: Subject to any disclaimer, the term of this patent is extended or adjusted under 35 U.S.C. 154(b) by 0 days.

(21) Appl. No.: 12/738,978

(22) PCT Filed: Oct. 31, 2008

(86) PCT No.: PCT/US2008/082091
§ 371 (c)(1),
(2), (4) Date: Apr. 20, 2010

(87) PCT Pub. No.: WO2009/059210

PCT Pub. Date: May 7, 2009

(65) Prior Publication Data

US 2010/0267004 A1    Oct. 21, 2010

Related U.S. Application Data

(60) Provisional application No. 60/984,308, filed on Oct. 31, 2007.

(51) Int. Cl.
*C12Q 1/68* (2006.01)
*G01N 33/53* (2006.01)
*C07H 21/00* (2006.01)
*C07H 19/04* (2006.01)
*B01L 3/00* (2006.01)
*C12Q 1/70* (2006.01)

(52) U.S. Cl. ................ 435/6; 435/5; 435/7.1; 435/7.2; 536/25.32; 536/26.6; 422/61

(58) Field of Classification Search ............ 435/5, 435/6, 7.1, 7.2; 536/25.32, 26.6; 422/61
See application file for complete search history.

(56) References Cited

U.S. PATENT DOCUMENTS

2005/0203289 A1    9/2005    Schwartz et al.
2007/0004012 A1    1/2007    Sasikekharan et al.

OTHER PUBLICATIONS

Bioventures, Inc. et al., International Search Report and Written Opinion, PCT/US08/82091, Feb. 13, 2009.
Bioventures, Inc. et al., International Preliminary Report on Patentability, PCT/US08/82091, Feb. 18, 2010.

*Primary Examiner*—Jezia Riley
(74) *Attorney, Agent, or Firm*—David A. Farah; Sheldon Mak & Anderson

(57) ABSTRACT

A method for labeling biological molecules and synthetic molecules that contain a geminal diol, such as RNA, carbohydrates or glycoproteins, using a periodate sequestering agent is provided. Compositions and kits for use in the labeling method are also provided.

26 Claims, 3 Drawing Sheets

METHOD, SUBSTANCES AND KITS FOR LABELING POPULATION OF RNA AND OTHER SUBSTANCES CONTAINING VICINAL DIOLS

CROSS-REFERENCE TO RELATED APPLICATION

The present Application is a national stage of International Patent Application No. PCT/US2008/082091, titled "Method, Substances and Kits for Labeling Populations of RNA and Other Substances Containing Vicinal Diols," filed Oct. 31, 2008, which claims priority from U.S. Provisional Patent Application Ser. No. 60/984,308, titled "Method, Substances and Kits for Labeling Populations of RNA and Other Substances Containing Geminal Diols," filed Oct. 31, 2007, the contents of which are incorporated in this disclosure by reference in their entirety.

BACKGROUND

Frequently it is necessary to label molecules in order to provide a means of detecting and measuring the presence or absence of molecular entities, especially for the detection of biological molecules, chemical species and even certain types of organisms or cells. One of the trends to improve efficiency of identifying and quantifying these molecular or cellular entities is to perform multiplex types of analyses where the objective is to measure many of these species in a single assay such as microarrays or flow cytometric assays.

Presently RNA species within a specimen are isolated and usually converted to their respective cDNAs for analysis by microarrays, quantitative real-time RT-PCR and other methods well known in the art. Many of these methods are time consuming, and suffer from sample losses during the various isolation and repeated purification steps required to be performed to obtain a result. In particular many of the labeling agents presently used are very reactive and prone to decomposition especially in aqueous solutions and substantial excess of labeling agents relative to the species to be labeled are frequently required for successful labeling. This is particularly the case for N-hydroxysuccinimide esters which are well known to be labile in aqueous media and have half-lives of only a few minutes. More importantly, these esters generally are used to modify primary amines, consequently if target substances lack this functionality they must me modified to provide a free amine, thus adding additional steps to the labeling process and usually requiring additional steps of purification leading to loss of some sample. Likewise maleimides also suffer the same disadvantages with respect to their reactions with sulfhydryl groups. For example, methods presently described in the art rely on sequential reaction of the RNA or geminal diol containing species such as polysaccharides or glycosylated proteins or peptides with periodate, usually neutralization of the periodate with glycerol followed by separation of the oxidized RNA or resulting geminal aldehyde species of interest from the periodate to prevent reaction of periodate with the labeling moiety by for example ethanol precipitation, exclusion chromatography and the like. The isolated oxidized RNA or geminal aldehyde reaction product is then reacted with a hydrazide containing signal moiety and a second physical separation of the labeled RNA or geminal aldehyde species is performed such as ethanol precipitation, or chromatography. Because periodate is usually employed in the periodate reaction of geminal hydroxyl groups, the scavenging of periodate with glycerol is ineffective in removing the periodate, merely diverting the reaction to another species yet introducing promiscuous dialdehydes to the reaction which can consume significant portions of the labeling agent with consequent diversion to unproductive labeling of irrelevant species, namely the geminal aldehydes arising from the oxidation of glycerol or other geminal diol containing scavengers. There is a need for rapid labeling methods without these limitations.

SUMMARY

One embodiment of the present invention is a method for labeling substance that contains geminal diols, such as as RNA, carbohydrates, glycosylated proteins and the like. According to the method, first, a geminal diol containing substance is provided. Then, a periodate salt is added to the geminal diol containing substance. The geminal diol containing substance is capable of being oxidized with periodate to produce an aldehyde containing substance. An alkaline earth metal salt is then added, as well as a signal label, where the signal label is capable of reaction with the aldehyde containing substance, to produce a signal labeled substance. The method may further comprise separating the signal labeled substance, and/or analysis of the signal labeled substance.

In a preferred embodiment, the alkaline earth metal salt is a barium salt, more preferably, the alkaline earth metal salt is barium acetate, separately added, or generated in situ. In other preferred embodiments, the geminal diol containing substance is one, or a combination of an RNA, a protein, a streptavidin and an avidin.

In another preferred embodiment of the method of the invention, the signal label is a hydrazide containing moiety comprising the nitrogen linkage —NH—NH$_2$, and the hydrazide containing moiety is attached to a suitable label. More preferably, the hydrazide containing signal moiety is selected from the group consisting of hydrazides, semicarbazides, carbohydrazides, and hydroxylamine derivatives, and the label of the signal label is selected from the group consisting of enzymes, fluorescent labels, chemiluminescent labels, electroluminescent labels, and biotin.

Another embodiment of the present invention is a composition for use in the labeling method of the invention. According one embodiment, the composition comprises an aqueous carrier and an alkaline earth metal salt, preferably, the alkaline earth metal salt is a barium salt. The composition may also comprise a signal label capable of reaction with an aldehyde containing substance, preferably a hydrazide containing moiety as described herein.

In another embodiment, a kit is provided with one or more reagents for use in the labeling method of the invention. According to one embodiment, the kit comprises one or more of the following reagents selected from the group consisting of a periodate salt, an alkaline earth metal salt, and a signal label capable of reaction with an aldehyde containing substance, wherein the reagents are in their elemental form or provided in an aqueous solution. The kit may also comprise one or more aqueous buffers. According to another embodiment, the kit for use in a method for labeling a substance that contains a geminal diol comprises an alkaline earth metal salt and instructions for labeling a substance that contains a geminal diol. The kit may also comprise a periodate salt, and/or a signal label capable of reaction with an aldehyde containing substance.

FIGURES

These and other features, aspects and advantages of the present invention will become better understood from the following description, appended claims, and accompanying figures where:

DESCRIPTION

Figure 1:
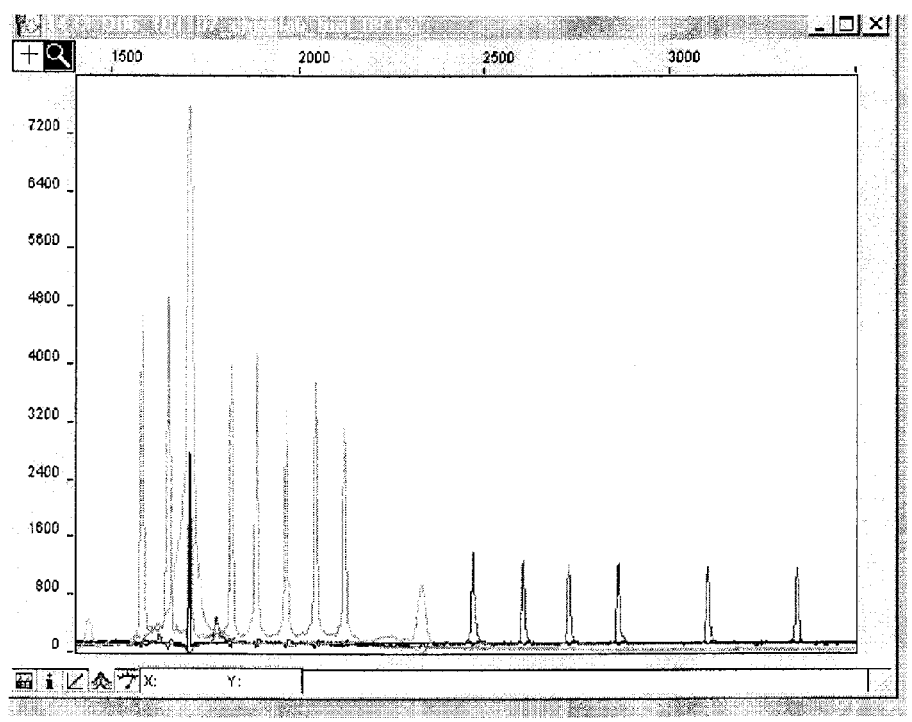
FIG. 1 is a graph showing the results of the labeling reaction of the RNA sequence, hsa-let-7e according to one embodiment of the present invention.

According to one embodiment, the invention comprises a method for labeling a substance that contains geminal diols. According to the method, we have found that periodate salts in conjunction with a periodate-sequestering-agent and fluorescent hydrazides and related compounds can label geminal diol containing compounds, such as RNA and glycosylated substances such as proteins, rapidly and efficiently without degradation in a very rapid process. Separation of the geminal diol containing compounds containing the hydrazide label requires only a brief centrifugal passage over a separation column.

The method and reagents disclosed herein are distinguished over methods presently described in the art. Such known methods rely on sequential reaction of the RNA or geminal diol containing species with periodate, usually neutralization of the periodate with glycerol, which is then followed by separation of the oxidized RNA or resulting geminal aldehyde species of interest from the periodate to prevent reaction of periodate with the labeling moiety by for example ethanol precipitation, exclusion chromatography and the like. The isolated oxidized RNA or geminal aldehyde reaction product is then reacted with a hydrazide containing signal moiety and a second physical separation of the labeled RNA or geminal aldehyde species is performed such as ethanol precipitation, or chromatography. The scavenging of periodate with glycerol is ineffective in removing the periodate, merely diverting the reaction to another species yet introducing promiscuous dialdehydes to the reaction which can consume significant portions of the labeling agent and diverting the reaction products to unproductive labeling of irrelevant species, namely the geminal aldehydes arising from the oxidation of glycerol.

The simplicity and superiority of the method and substances described herein over the current art will be made clear by the following description and examples.

Referring now to Scheme I below, one embodiment of the invention, a method for labeling a geminal diol containing substance is shown. As shown in Scheme I, first, a geminal diol containing substance (1) capable of being oxidized with periodate is provided. Then, a periodate salt (2) is added to the geminal diol containing substance (1), followed by the addition of a periodate sequestering agent (M+X−, 3), such as a barium salt. The reaction is allowed to proceed and the periodate salt (2) is allowed to cleave the geminal diol containing substance into a resulting di-aldehyde (4). Then, a signal label containing moiety, such as a signal molecule containing at least one functional group capable of reaction with aldehydes (N-label, 5) is then added to the di-aldehyde (4). The resulting labeled substance (6) may then be separated and analyzed according to known methods.

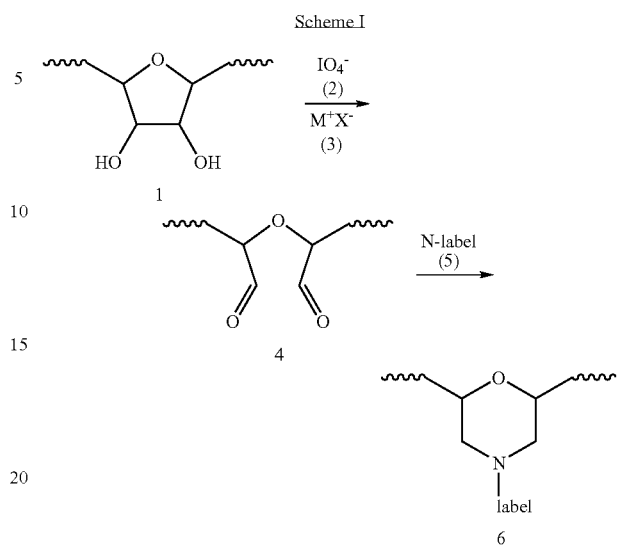

The alkaline earth metal salt (M+X−) is added to the reaction mixture in an amount such that the concentration of metal anions and the initial concentration of periodate ions are substantially equal. To assure complete sequestering of periodate ions and iodate ions arising from the oxidation of the diols, the metal ions are in slight excess of 2%-20%, preferably on the order of 5%-10% molar excess to periodate and iodate ions.

In a preferred embodiment the alkaline earth metal is barium, such as in barium salts including barium chloride and barium acetate. The alkaline earth metal salt may be mixed, such as by the addition of barium chloride and sodium acetate to the reaction, a mixed alkaline earth metal solution, and combinations thereof. Alternately, one alkaline earth metal salt may be used according to the invention. Preferably, the alkaline earth metal salt is soluble, or at least partially soluble in the reaction mixture.

The signal label containing moiety is a molecule containing at least one functional group capable of reaction with aldehydes (N-label, 5) are known in the art, for example primary amines, a hydrazides, semihydrazides, carbohydrazides, thiocarbazides, and hydroxylamines are examples of functional groups which can react with aldehydes. The term hydrazide, as used herein, describes hydrazide containing moieties, i.e., compounds containing the nitrogen linkage —NH—NH$_2$, such as hydrazides, semicarbazides and carbohydrazides, as well as hydroxylamine derivatives attached to suitable labels. Those skilled in the art will recognize that a variety of hydrazides are useful for the purposes set forth herein.

The signal component, or "label" of the signal molecule may be at least one of the group consisting of enzymes, fluorecent labels, chemiluminescent labels, electroluminescent labels, and other labels known in the art such as biotin.

According to one embodiment, the signal label is added to the alkaline earth metal treated reaction mixture without physical separation of the periodate from the oxidized nucleic acid or geminal aldehyde reaction product. For example, the signal label may be added directly to the alkaline earth metal treated reaction mixture, usually in the range of 0.5 ug-4 ug of labeling agent in a volume of 1-5 ul of suitable solvent, usually aqueous media. The labeling reaction is allowed to proceed for a period of one minute to one hour, more usually from 5 minutes to 15 minutes at ambient temperature. The reaction can be accelerated by the application of heat usually 37° C., but those skilled in the art will recognize that other temperatures or times can be utilized based on the nature and physical properties of the species being labeled and their compatibility with other times and temperatures According to another embodiment, the invention is a method for labeling RNA, as shown in Scheme II. The method comprises first, providing a sample of RNA (7), total or fractionated into subpopulations. The RNA (7) is treated with a periodate salt (8) in buffered aqueous media, followed by the addition of a soluble barium salt (9). The reaction is allowed to proceed to produce the resultant aldehyde (10) The hydrazide containing label (label-hydrazide, 11) is then allowed to react with the aldehyde (10). The reaction between the label-hydrazide (11) and the aldehyde (10) is allowed to proceed, producing labeled RNAs (12). The labeled RNAs (12) may be separated from the other reaction components by a brief centrifugation of the reaction mixture over a molecular size fractionation column. The labeled RNAs (12) obtained are suitable for use in microarrays, flow analysis and fluorescent capillary electrophoresis as well as other methods well known in the art.

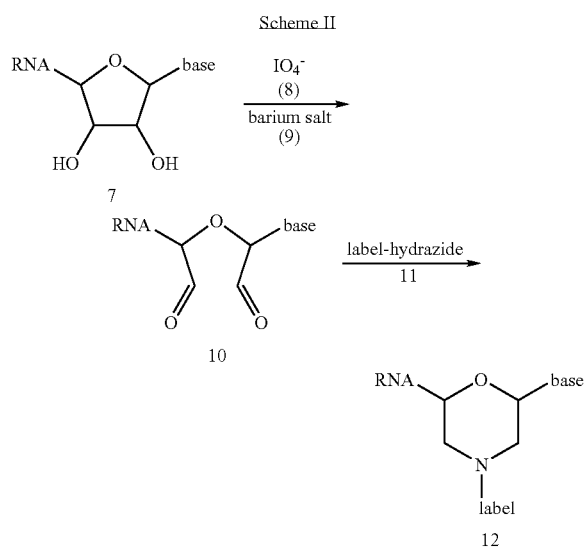

The RNA sample or other sample of geminal diol containing substance used according to the invention may be obtained from a biological source such as microorganisms, plants and animals by methods well known in the art. For example, there are a number of kits designed to isolate total RNA or sub-fractions such as messenger RNAs, microRNAs and ribosomal RNAs which can be obtained from vendors such as Qiagen, Invitrogen and Ambion indicate but a few such suppliers. RNA suitable for the labeling method set forth should be in either water, deionized formamide or amine free buffers such as phosphate buffered saline, citrate, MES, MOPS, HEPES, acetate and the like usually at neutral pH or alternatively the RNA can be in a dry or lyophilized from provide that there are no free primary amines present.

The RNA solution may be used in a small volume such as 0.5 ul-10 ul and usually in the quantity of 0.5-10 ug of RNA. Dry RNA may be brought into solution with water or the reaction buffer described below. The RNA to be labeled is then brought into contact with a solution of a periodate salt, usually sodium or potassium salt at a concentration of between 1 mM and 100 mM such that the final periodate concentration is between 0.1 and 10 mM in the combined solutions of RNA and periodate. The periodate salt may be dissolved in water. The reaction is buffered to a pH of 4.0-8.0, preferably between pH 4.5 and 7.2. For example MES buffer pH 4.7 in the range of 0.1M-0.01M is added. Likewise acetate buffers over similar concentration and pH ranges can be utilized. The reaction is then incubated at a temperature between 20° C. and 50° C., usually for convenience at ambient temperatures near ~25° C. The time of incubation is from 5 minutes to 1 hour usually between 15 minutes and 30 minutes, preferably protected from light. Following incubation an amount of an aqueous solution of an alkaline earth metal salt, such as barium chloride or barium acetate is added to the reaction mixture, such that the concentration of barium ions and the initial concentration of periodate ions are substantially equal. To assure complete sequestering of periodate ions and iodate ions arising from the oxidation of the diols, barium is in slight excess of 2%-20%, preferably on the order of 5%-10% molar excess to periodate and iodate ions. Preferably, the barium salt is barium acetate.

The label-hydrazide may be added to the reaction mixture without isolation of the aldehyde reaction product. For example, fluorescein hydrazide may be added to the barium treated reaction mixture without physical separation of the periodate from the oxidized nucleic acid or geminal aldehyde reaction product. More specifically, fluorescein carbohydrazide may be added directly to the barium treated reaction mixture, usually in the range of 0.5 ug-4 ug of labeling agent in a volume of 1-5 ul of suitable solvent, usually aqueous media. The labeling reaction is allowed to proceed for a period of one minute to one hour, more usually from 5 minutes to 15 minutes at ambient temperature, or may be accelerated by the application of heat, usually 37° C. However, those skilled in the art will recognize that other temperatures or times can be utilized based on the nature and physical properties of the species being labeled and their compatibility with other times and temperatures.

According to another embodiment, the invention comprises a composition for use according to the method described herein. In one embodiment the composition comprises a periodate salt and a buffered aqueous media. In another embodiment, the composition comprises an alkaline earth metal salt and a signal label. Preferably, the soluble alkaline earth metal salt is a barium salt.

According to another embodiment, the invention comprises a kit for use in the method described herein. The kit comprises one or more than reagent for use the in the method of the invention. Preferably the kit comprises one or more of the following reagents selected from a periodate salt, a buffered aqueous media, an alkaline earth metal salt, and a signal label. Preferably, the alkaline earth metal salt is soluble, or solubilized in the reaction mixture, and preferably, the alkaline earth metal salt is a barium salt, more preferably barium acetate. Preferably, the signal label is a hydrazide containing signal label, capable of reaction with an aldehyde.

The compositions, methods and systems described herein may include other materials and/or modifications as necessary as will be understood by those of skill in the art by reference to this disclosure and the invention is understood not to be limited by the foregoing examples.

EXAMPLES

Example 1

Hydrazide Labeling of RNA Using Periodiate Oxidation

Synthetic miRNA

The synthetic miRNA (syn-miRNA) were selected and designed to specifically reflect a set of human miRNAs. The syn-miRNA were obtained from Integrated DNA Technologies (Coralville, Iowa). Each syn-miRNA was resuspended a stabilization buffer containing 1 mM Sodium Citrate (Ambion; Austin, Tex.) and 30% deionized formamide (Bioventures; Murfreesboro, Tenn.) to a final concentration of 100 pmol/ul. The syn-miRNA's were then aliquoted into 10 ul working stocks in 0.5 ml tubes (Nalgene; Rochester, N.Y.). The names and sequences of the RNA sequences used in the following examples are shown below in Table 1.

TABLE 1

| NAME | SEQUENCE | SEQ ID NO: |
|---|---|---|
| hsa-let-7a | /5Phos/rUrGrArGrGrUrArGrUrArGrGrUrUrGrUrArUrArGrUrU | SEQ ID NO: 1 |
| hsa-let-7e | /5Phos/rUrGrArGrGrUrArGrGrArGrGrUrUrGrUrArUrArGrU | SEQ ID NO: 2 |
| hsa-miR-106a | /5Phos/rArArArArGrUrGrCrUrUrArCrArGrUrGrCrArGrGrUrArGrC | SEQ ID NO: 3 |
| hsa-miR-126* | /5Phos/rCrArUrUrArUrUrArCrUrUrUrGrGrUrArCrGrCrG | SEQ ID NO: 4 |
| hsa-miR-135a | /5Phos/rUrArGrGrCrUrUrUrUrArUrUrCrCrUrArUrGrUrGrA | SEQ ID NO: 5 |
| hsa-miR-138 | /5Phos/rArGrCrUrGrGrUrGrUrUrGrUrGrArArUrC | SEQ ID NO: 6 |
| hsa-miR-154 | /5Phos/rUrArGrGrUrUrArUrCrCrGrUrGrUrUrGrCrCrUrUrCrG | SEQ ID NO: 7 |
| hsa-miR-154* | /5Phos/rArArUrCrArUrArCrArCrGrGrUrUrGrArCrCrUrArUrU | SEQ ID NO: 8 |

Yeast tRNA

Purified Yeast tRNA was obtained from Ambion; Austin, Tex.).

Periodate Oxidation and Hydrazide Labeling

Oxidation was carried out by adding an oxidation mix to each well of a Bio-Rad 96-well Multiplate consisting of 100 mM Sodium Periodate (Sigma Chemical Co; St. Louis, Mo.) and 100 mM MES (2-(N-morpholino)ethanesulfonic acid), pH 4.7 (Sigma Chemical Co), to 20 pmol of hsa-miR-7e in well A1 of a Bio-Rad 96-well Multiplate, 2 ug of yeast tRNA in well B1 and in C1 no RNA for a final volume of 9 ul.

The plate was then briefly pulsed in a centrifuge to mix components and placed in the dark at room temperature for 30 minutes. After 30 minutes 0.55 ul of 100 mM Barium Chloride (Sigma Chemical Co.) was added to each well followed by adding 0.45 ul of 10 ug/ul FAM-5-thiosemicarbozide (Anaspec, Inc.; San Jose, Calif.). The plate was then briefly pulsed in a centrifuge to mix components and placed in the dark at room temperature for 15 minutes.

Labeling Reaction Clean-Up

After 15 minutes of the labeling of the RNAs, Micro Select-D, G25 TE (IBI-Shelton SCIENTIFIC; Peosta, Iowa) were used to remove the unreacted dye. The Micro Select-D columns were placed in a 2 ml collection tubes (IBI-Shelton SCIENTIFIC). The column/collection tubes were placed in a microcentrifuge, IEC MicromaxRX (Thermo Scientific; Waltham, Mass.) and spun at 1,000×g for 2 minutes to remove the hydrating fluid. The columns were then placed into a new 2 ml collection tubes and the reaction mixture was loaded onto the column being careful not to disturb the column resin. After 3 minutes the column/collection tubes were placed in the microcentrifuge (Thermo Scientific) and spun at 1,000×g for 5 minutes to collect the purified labeled RNA.

An additional cleanup to remove any unreacted dye was carried out by ethanol precipitation. 2 ul of 3M Sodium Acetate, 300 ul of 100% Ethanol and 1 ul of glycogen was added to each reaction tube then placed at −80° C. overnight. Tubes were spun at 12,000×g for 30 minutes at 4° C. to pellet the RNA, the ethanol was then drawn off and discarded. The pellet was washed with 200 ul of 95% ethanol, vortexed briefly then spun tubes at 12,000×g for 30 minutes at 4° C. to pellet the RNA, and the ethanol was drawn off and the ethanol wash was repeated one additional time. After drawing off the ethanol from the last wash the tubes were placed in a Speed-Vac (Sorvall) at low temperature for 10 minutes to evaporate any remaining ethanol. After the samples were dried, 20 ul of sterile water was added to resuspend the recovered labeled samples (RNAs).

Analysis of the microRNA Labeling 1 ul of the cleaned labeled product was added to a 96-well Multiplate (Bio-Rad) containing 18.5 ul DI Formamide (Bio-Ventures, Inc., Murfreesboro, Tenn.) and 0.5 ul of 20 fmol each of Hex labeled oligonucleotides (BioVentures, Inc., Murfreesboro, Tenn.) ranging in size from 15 bp, 20 bp, 25 bp, 30 bp, 35 bp, 40 bp, 45 bp, 50 bp. The plate was then briefly pulsed in a centrifuge, Allegra 31 (Beckman Coulter; Fullerton, Calif.) to mix components then placed on an ABI Prism® 3100 DNA Analyzer (Applied Biosystems; Foster City, Calif.) and were analyzed using the Genescan program, Dye Set "D," module file "GeneScan_030507_microshort," with an injection voltage of 1 kvolt, injection time of 22 seconds and a run times of 1000 seconds. The raw data was analyzed using GeneScan software (Applied Biosystems).

Figure 2:
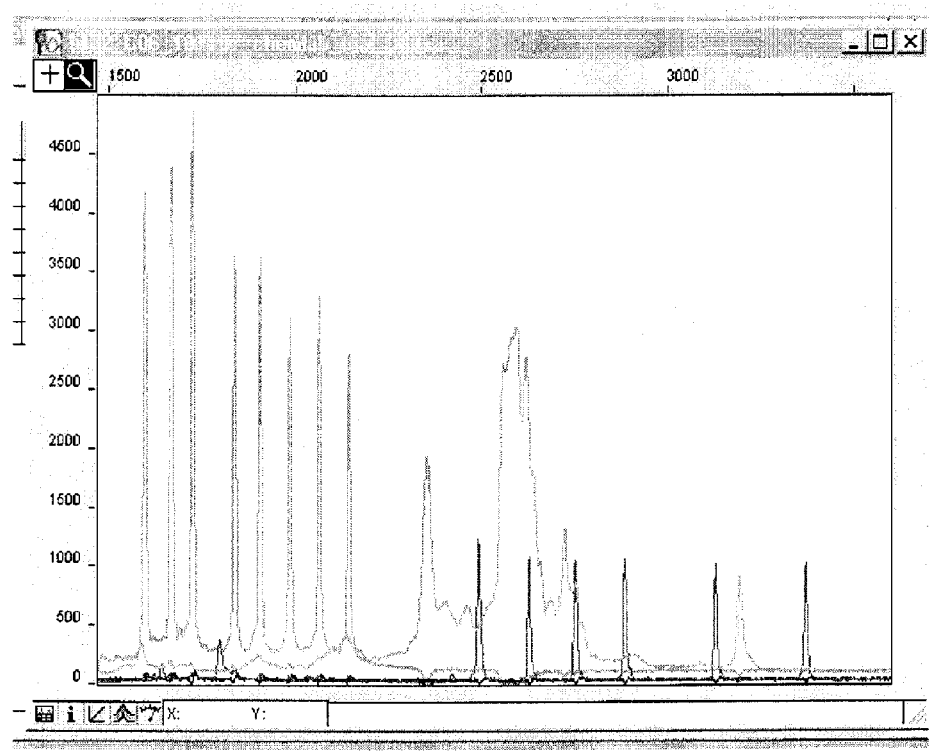
FIG. 2 is a graph showing the results of the labeling reaction of a yeast RNA according to another embodiment of the present invention.
Figure 3:
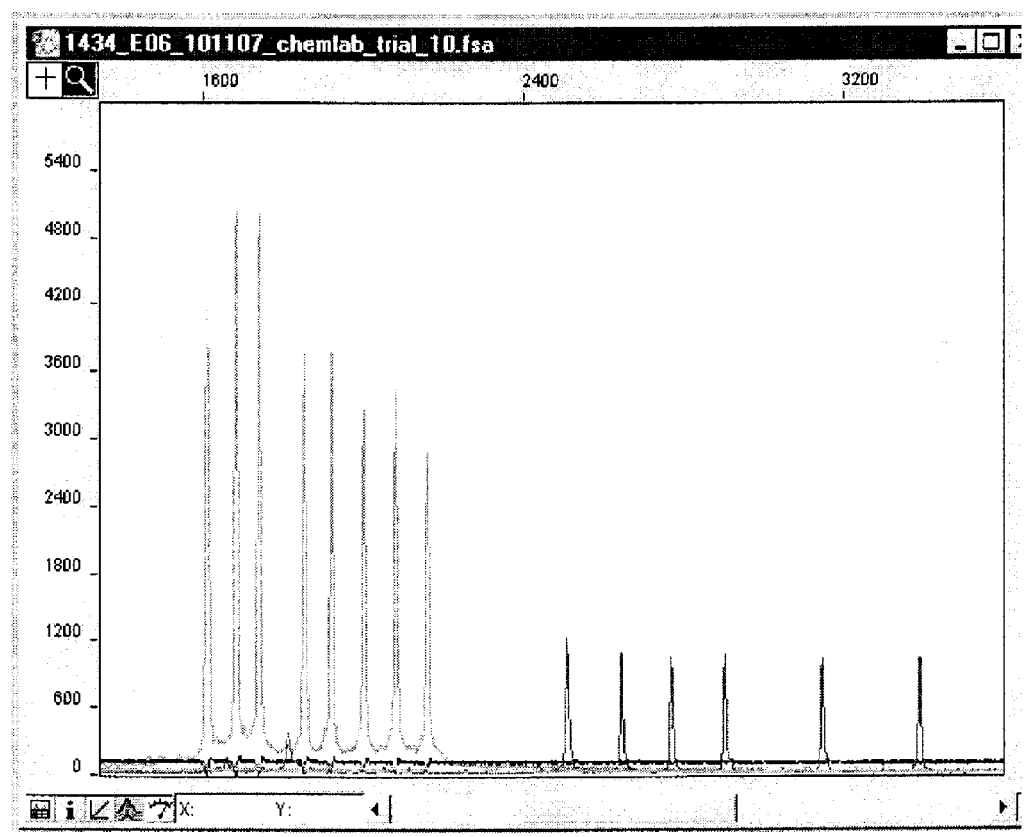
FIG. 3 is a graph showing the labeling reaction components only, no microRNA, according to another embodiment of the present invention.

Referring now to FIG. 1, a plot of the results of the labeling reaction of the RNA sequence, hsa-let-7e, a sequence of 24 by in length is shown. Referring now to FIG. 2, a plot of the results of the labeling reaction of yeast tRNA, of a sequence approximatly 80 bp in length is shown. Referring now to FIG. 3, a plot of the results of the labeling reaction components only, no microRNA is shown. The results of the electrophoretic analysis of the labeled reaction products, as shown in FIGS. 1-3, indicated that the chemical labeling was completed and the products migrated at their expected fragment size while there was no evidence of any labeling when RNA was not present.

Example 2

Hydrazide Labeling of RNA Using Periodiate Oxidation (Acetate Method)

Synthetic miRNA

The synthetic RNAs and yeast tRNAs as used in example one were utilized as follows.

Periodate Oxidation and Hydrazide Labeling

Oxidation was carried out by adding periodate buffer [(1 mM final reaction concentration Sodium Periodate (Sigma Chemical Co; St. Louis, Mo.) and 1 mM final reaction concentration Sodium Acetate, pH 5.7 (Sigma Chemical Co)], to either 20 pmol of hsa-miR-7a or 2 ug of yeast tRNA in a Bio-Rad 96-well Multiplate to a final volume of 9 ul. The plate was then briefly pulsed in a centrifuge to mix components and placed in the dark at room temperature for 30 minutes. After 30 minutes 0.55 ul of 10 mM Barium Chloride, brought into solution in 100 mM Sodium Acetate (Sigma Chemical Co.) was added to each reaction well. Following the barium addition, 0.45 ul of 1 ug/ul FAM-5-thiosemicarbozide (Anaspec, Inc.; San Jose, Calif.) brought up in Dimethylformamide (Sigma Chemical Corp., Saint Louis, Mo.) was added to each reaction well. The plate was then briefly pulsed in a centrifuge to mix components and placed in the dark at room temperature for 15 minutes.

Labeling Reaction Clean-Up

After the labeling of the RNAs, Micro spin columns (Thermo Scientific; Pittsburgh, Pa.) packed with 0.06 g Sephadex G25 and hydrated with 300 ul 1× Tris-EDTA were used to remove the uncoupled dye. The Micro spin columns were placed in a 1.5 ml collection tubes (USA/Scientific; Ocela, Fla.). The column/collection tubes were placed in a microcentrifuge, IEC MicromaxRX (Thermo Scientific; Waltham, Mass.) and spun at 1,200×g for 5 minutes to remove the hydrating fluid. The columns were then placed into new 1.5 ml collection tubes and the sample was loaded onto the column being careful not to disturb the column resin. After 3 minutes the column/collection tubes were placed in the microcentrifuge and spun at 1,200×g for 5 minutes to collect the purified labeled RNA samples.

Analysis of the microRNA Labeling 1 ul of the cleaned labeled product was added to a new 96-well Multiplate (Bio-Rad) containing 18.5 ul DI Formamide (BioVentures Inc., Murfreesboro, Tenn.) and 0.5 ul of 20 fmol each of Hex labeled oligonucleotides (BioVentures, Inc.) ranging in size from 15 bp, 20 bp, 25 bp, 30 bp, 35 bp, 40 bp, 45 bp, 50 bp. The plate was then briefly pulsed in a centrifuge, Allegra 31 (Beckman Coulter; Fullerton, Calif.) to mix components then placed on an ABI Prism® 3100 DNA Analyzer (Applied Biosystems; Foster City, Calif.) and were analyzed using the Genescan program, Dye Set "D," module file "GeneScan__030507_microshort," with an injection voltage of 1 kvolt, injection time of 22 seconds and a run times of 1000 seconds. The raw data was analyzed using GeneScan software (Applied Biosystems).

Figure 4:
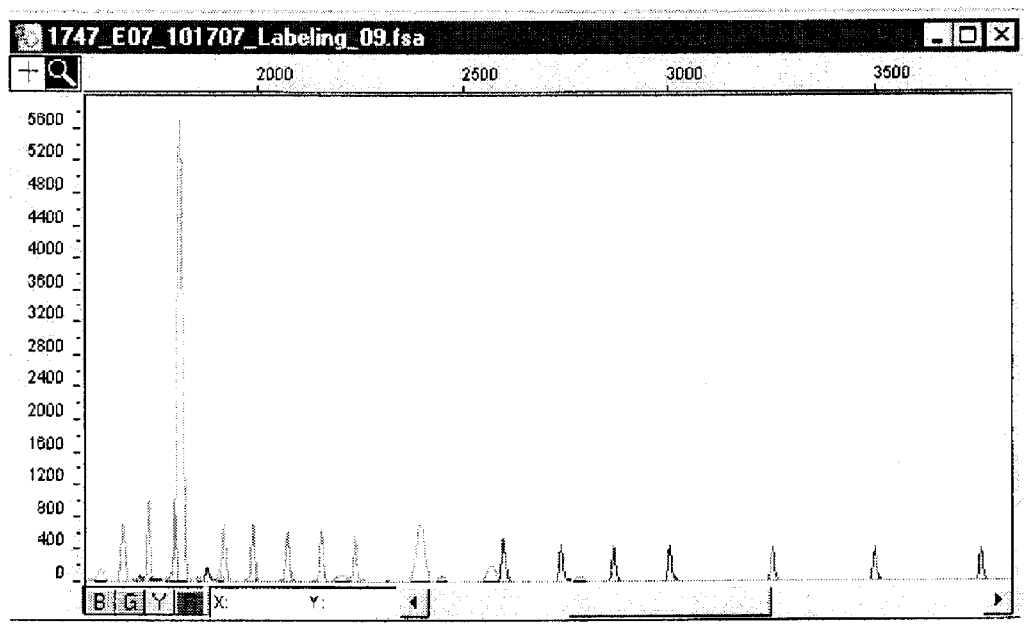
FIG. 4 is a graph showing the results of the labeling reaction of the RNA sequence, hsa-let-7a according to one embodiment of the present invention.
Figure 5:
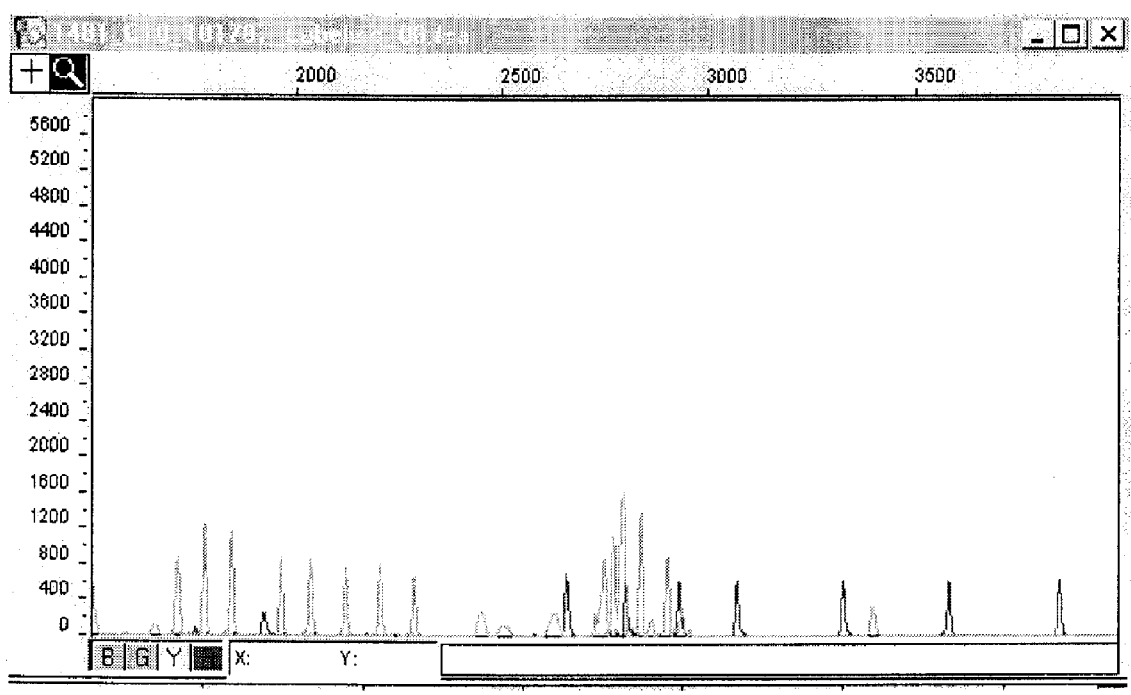
FIG. 5 is a graph showing the results of the labeling reaction of a yeast RNA sequence according to one embodiment of the present invention.
Figure 1:
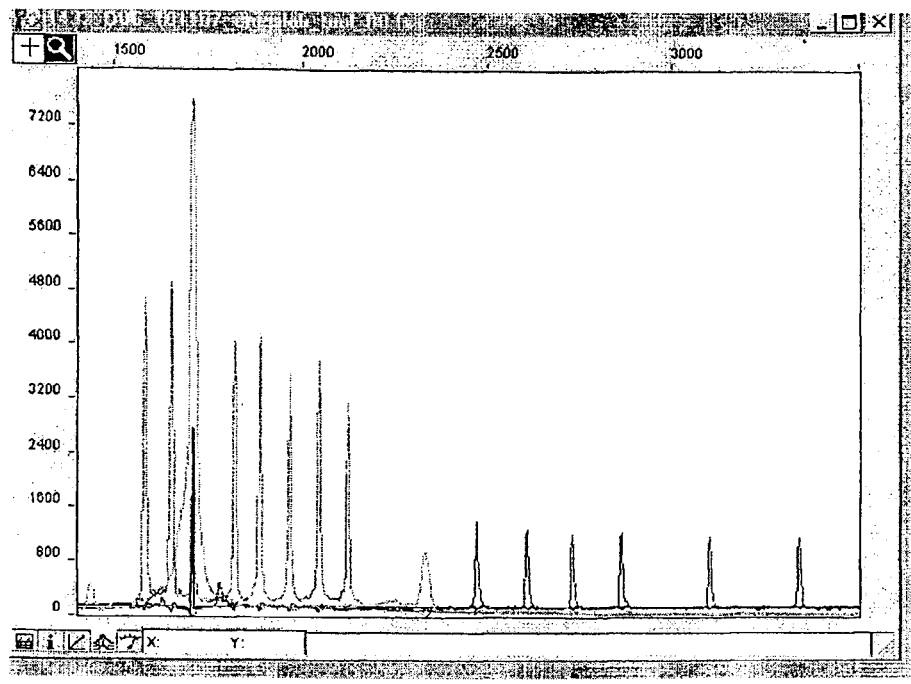
Figure 2:
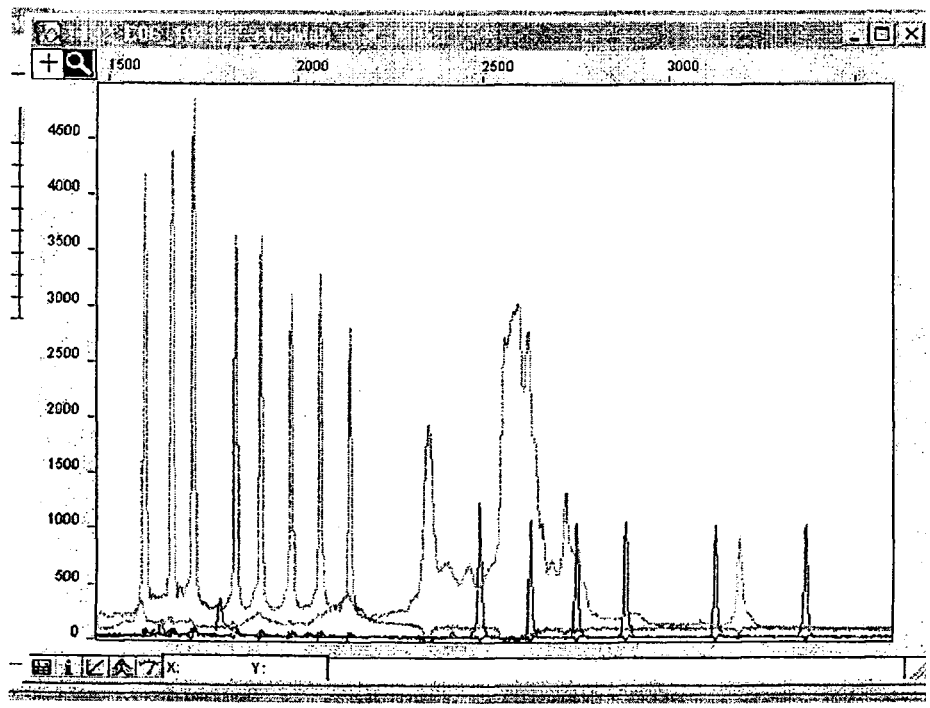
Figure 3:
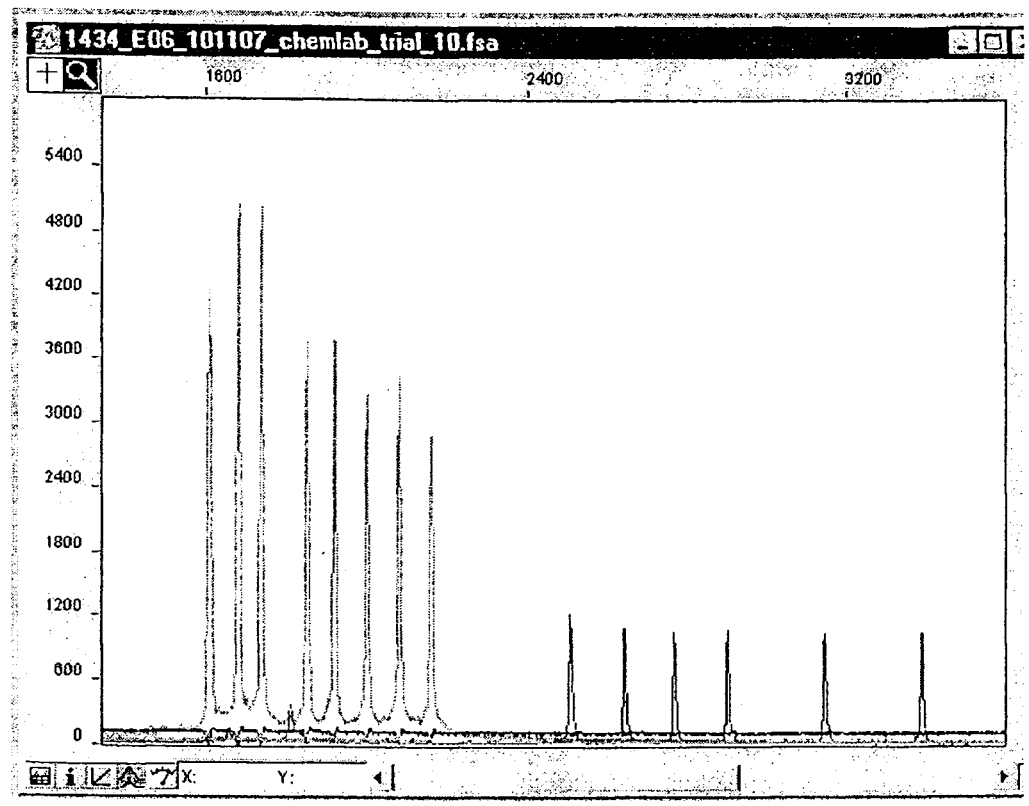
Figure 4:
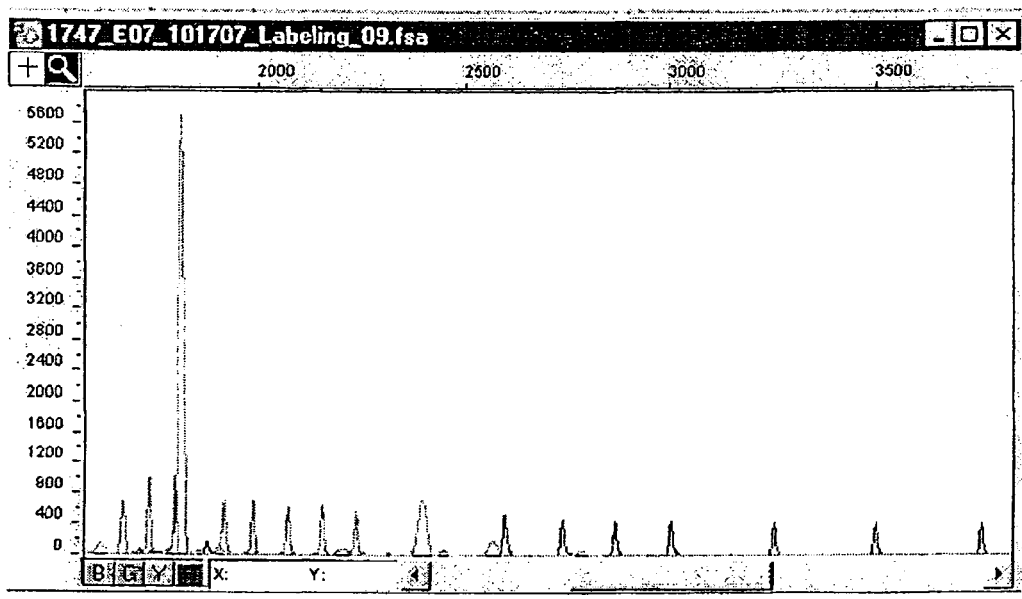
Figure 5:
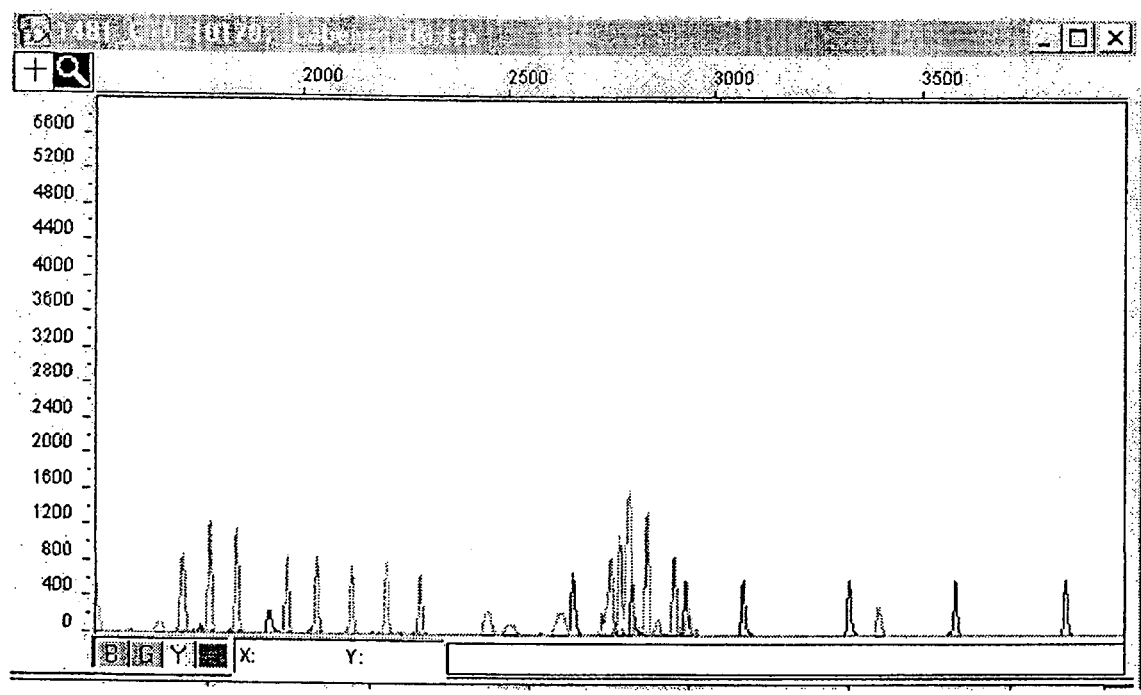

Referring now to FIG. 4, a plot of the results of the labeling reaction of the RNA sequence hsa-let-7a, an RNA sequence of 24 by in length is shown. Referring now to FIG. 5, a plot of the results of the labeling reaction of yeast tRNA, an RNA sequence of approximately 80 bp (multiplet) in length is shown. The results of the electrophoretic analysis of the labeled reaction products, as shown in FIGS. 4 and 5, demonstrated that the chemical labeling was completed and the products migrated at their expected fragment size while there was no evidence of any labeling when RNA was not present.

Example 3

Hydrazide Labeling of Streptavidin/Avidin Using Periodiate Oxidation

Preparation of Streptavidin and Avidin

Streptavidin (Roche Applied Science; Indianapolis, Ind.) was brought into solution in 0.5% Sodium Azide to a final concentration of 1 mg/ml and Avidin (Sigma Chemical Co; St. Louis, Mo.) was brought into solution in 0.5% Sodium Azide for a final concentration of 1 mg/ml.

Periodate Oxidation and Hydrazide Labeling

Oxidation of Streptavidin and avidin prepared above was carried out by adding periodate buffer [(1 mM final reaction concentration Sodium Periodate (Sigma Chemical Co; St. Louis, Mo.) and 1 mM final reaction concentration Sodium Acetate, pH 5.7 (Sigma Chemical Co)], to each of 1 ul of Streptavidin, 1 ul of Avidin, or 1 ul of sterile water in a Bio-Rad 96-well Multiplate to a final volume of 9 ul.

The plate was then briefly pulsed in a centrifuge to mix components and placed in the dark at room temperature for 30 minutes. After 30 minutes 0.55 ul of 10 mM Barium Chloride, brought into solution in 100 mM Sodium Acetate (Sigma Chemical Co.) was added to each reaction well. Following the barium addition, 0.45 ul of 1 ug/ul FAM-5-thiosemicarbozide (Anaspec, Inc.; San Jose, Calif.) brought up in Dimethylformamide (Sigma Chemical Corp.) was added to each reaction well. The plate was then briefly pulsed in a centrifuge to mix components and placed in the dark at room temperature for 15 minutes.

Labeling Reaction Clean-Up

After the labeling of the samples, Micro spin columns (Thermo Scientific; Pittsburgh, Pa.) packed with 0.06 g Sephadex G25 and hydrated with 300 ul 1× Tris-EDTA were used to remove the uncoupled dye. The Micro spin columns were placed in a 1.5 ml collection tubes (USA/Scientific; Ocela, Fla.). The column/collection tubes were placed in a microcentrifuge, IEC MicromaxRX (Thermo Scientific; Waltham, Mass.) and spun at 1,200×g for 5 minutes to remove the hydrating fluid. The columns were then placed into new 1.5 ml collection tubes and the sample was loaded onto the column being careful not to disturb the column resin. After 3 minutes the column/collection tubes were placed in the microcentrifuge and spun at 1,200×g for 5 minutes to collect the purified labeled samples.

Analysis of the microRNA Labeling

The labeled reactions were analyzed by reading the fluorescence on a Nanodrop 3300 Fluorospectrometer (Nanodrop Technologies; Wilmington, Del.) measured using 470 nm excitation source with the emission wavelength monitored at 515 nm. The results were as follows:

Streptavidin labeling reaction gave a reading of 413.4 RFU's equivalent to 87.2 fmols Avidin labeling reaction gave a reading of 592.1 RFU's equivalent to 111.36 fmols No target control labeling reaction gave a reading of 51.2 RFU's equivalent to 17.7 fmols The labeled streptavidin was 5 times the amount of uncoupled dye and the avidin was 6 times the amount of uncoupled dye indicating that the proteins had been labeled by the dye.

Although the present invention has been discussed in considerable detail with reference to certain preferred embodiments, other embodiments are possible. Therefore, the scope of the appended claims should not be limited to the description of preferred embodiments contained herein.

SEQUENCE LISTING

<160> NUMBER OF SEQ ID NOS: 7

<210> SEQ ID NO 1
<211> LENGTH: 22
<212> TYPE: RNA
<213> ORGANISM: Artificial
<220> FEATURE:
<223> OTHER INFORMATION: Synthetic

<400> SEQUENCE: 1
ugagguagua gguuguauag uu                                              22

<210> SEQ ID NO 2
<211> LENGTH: 21
<212> TYPE: RNA
<213> ORGANISM: Artificial
<220> FEATURE:
<223> OTHER INFORMATION: Synthetic

<400> SEQUENCE: 2
ugagguagga gguuguauag u                                               21

<210> SEQ ID NO 3
<211> LENGTH: 24
<212> TYPE: RNA
<213> ORGANISM: Artificial
<220> FEATURE:
<223> OTHER INFORMATION: Synthetic

<400> SEQUENCE: 3
aaaagugcuu acagugcagg uagc                                            24

<210> SEQ ID NO 4
<211> LENGTH: 21
<212> TYPE: RNA
<213> ORGANISM: Artificial
<220> FEATURE:
<223> OTHER INFORMATION: Synthetic

<400> SEQUENCE: 4
cauuauuacu uuggacgc g                                                 21

<210> SEQ ID NO 5
<211> LENGTH: 23
<212> TYPE: RNA
<213> ORGANISM: Artificial
<220> FEATURE:
<223> OTHER INFORMATION: Synthetic

<400> SEQUENCE: 5
uauggcuuuu uauuccuaug uga                                             23

<210> SEQ ID NO 6
<211> LENGTH: 17
<212> TYPE: RNA
<213> ORGANISM: Artificial
<220> FEATURE:
<223> OTHER INFORMATION: Synthetic

<400> SEQUENCE: 6
agcugguguu gugaauc                                                    17

```
<210> SEQ ID NO 7
<211> LENGTH: 22
<212> TYPE: RNA
<213> ORGANISM: Artificial
<220> FEATURE:
<223> OTHER INFORMATION: Synthetic

<400> SEQUENCE: 7
uagguuaucc guguugccuu cg                                                  22
```

What is claimed is:

1. A method for labeling a substance that contains a geminal diol, the method comprising:
   (a) providing a geminal diol containing substance;
   (b) adding a periodate salt to the geminal diol containing substance, wherein the geminal diol containing substance is capable of being oxidized with periodate to produce an aldehyde containing substance;
   (c) adding an alkaline earth metal salt; and
   (d) adding a signal label, the signal label being capable of reaction with the aldehyde containing substance, to produce a signal labeled substance.

2. The method of claim 1 wherein the method further comprises separating the signal labeled substance.

3. The method of claim 1 wherein the method further comprises analysis of the signal labeled substance.

4. The method of claim 1 wherein the alkaline earth metal salt is a barium salt.

5. The method of claim 1 wherein the alkaline earth metal salt is barium acetate.

6. The method of claim 1 wherein the geminal diol containing substance is RNA.

7. The method of claim 1 wherein the geminal diol containing substance is a protein.

8. The method of claim 1 wherein the geminal diol containing substance is a streptavidin.

9. The method of claim 1 wherein the geminal diol containing substance is an avidin.

10. The method of claim 1 wherein the signal label is a hydrazide containing moiety comprising the nitrogen linkage —NH—NH$_2$, and wherein the hydrazide containing moiety is attached to a suitable label.

11. The method of claim 10 wherein the hydrazide containing signal moiety is selected from the group consisting of hydrazides, semicarbazides, carbohydrazides, and hydroxylamine derivatives.

12. The method of claim 1 wherein the label of the signal label is selected from the group consisting of enzymes, fluorescent labels, chemiluminescent labels, electroluminescent labels, and biotin.

13. The method of claim 12 wherein the label is a fluorescent label.

14. The method of claim 12 wherein the label is biotin.

15. The method of claim 1 wherein:
   (a) the geminal diol containing substance is a geminal diol containing RNA;
   (b) the periodate salt is added to the geminal diol containing RNA, wherein the geminal diol containing RNA is capable of being oxidized with periodate to produce an aldehyde containing RNA derivative;
   (c) the alkaline earth metal salt is added to the aldehyde containing RNA derivative; and
   (d) the signal label is capable of reaction with the aldehyde containing RNA, to produce a signal labeled RNA derivative.

16. The method of claim 15 wherein the alkaline earth metal salt is a barium salt.

17. A composition for use in the method of claim 1, the composition comprising
   an aqueous carrier; and
   an alkaline earth metal salt.

18. The composition of claim 17 wherein the alkaline earth metal salt is a barium salt.

19. The composition of claim 17, the composition further comprising a signal label capable of reaction with an aldehyde containing substance.

20. The composition of claim 19 wherein the signal label is a hydrazide containing moiety comprising the nitrogen linkage —NH—NH$_2$, and wherein the hydrazide containing moiety is attached to a suitable label.

21. A kit comprising one or more than reagent for use the in the method of claim 1.

22. The kit of claim 21, wherein the reagents comprise one or more of the following reagents selected from the group consisting of a periodate salt, an alkaline earth metal salt, and a signal label capable of reaction with an aldehyde containing substance, wherein the reagents are in their elemental form or provided in an aqueous solution.

23. The kit of claim 22 further comprising one or more aqueous buffers.

24. A kit for use in a method for labeling a substance that contains a geminal diol, the kit comprising:
   an alkaline earth metal salt; and
   instructions for labeling a substance that contains a geminal diol.

25. The kit of claim 24 further comprising a periodate salt.

26. The kit of claim 24 further comprising a signal label capable of reaction with an aldehyde containing substance.

* * * * *

UNITED STATES PATENT AND TRADEMARK OFFICE
CERTIFICATE OF CORRECTION

| | | |
|---|---|---|
| PATENT NO. | : 7,858,320 B2 | |
| APPLICATION NO. | : 12/738978 | |
| DATED | : December 28, 2010 | |
| INVENTOR(S) | : Dawson et al. | |

It is certified that error appears in the above-identified patent and that said Letters Patent is hereby corrected as shown below:

Please delete patent 7,858,320 in its entirety and insert patent 7,858,320 in its entirety as attached.

Signed and Sealed this
Twelfth Day of June, 2012

David J. Kappos
*Director of the United States Patent and Trademark Office*

(12) United States Patent
Dawson et al.

(10) Patent No.: US 7,858,320 B2
(45) Date of Patent: Dec. 28, 2010

(54) METHOD, SUBSTANCES AND KITS FOR LABELING POPULATIONS OF RNA AND OTHER SUBSTANCES CONTAINING VICINAL DIOLS

(75) Inventors: Elliott P. Dawson, Murfreesboro, TN (US); Kristie E. Womble, Franklin, TN (US)

(73) Assignee: BioVentures, Inc., Murfreesboro, TN (US)

( * ) Notice: Subject to any disclaimer, the term of this patent is extended or adjusted under 35 U.S.C. 154(b) by 0 days.

(21) Appl. No.: 12/738,978

(22) PCT Filed: Oct. 31, 2008

(86) PCT No.: PCT/US2008/082091

§ 371 (c)(1),
(2), (4) Date: Apr. 20, 2010

(87) PCT Pub. No.: WO2009/059210

PCT Pub. Date: May 7, 2009

(65) Prior Publication Data

US 2010/0267004 A1    Oct. 21, 2010

Related U.S. Application Data

(60) Provisional application No. 60/984,308, filed on Oct. 31, 2007.

(51) Int. Cl.
| | |
|---|---|
| C12Q 1/68 | (2006.01) |
| G01N 33/53 | (2006.01) |
| C07H 21/00 | (2006.01) |
| C07H 19/04 | (2006.01) |
| B01L 3/00 | (2006.01) |
| C12Q 1/70 | (2006.01) |

(52) U.S. Cl. .............. 435/6; 435/5; 435/7.1; 435/7.2; 536/25.32; 536/26.6; 422/61

(58) Field of Classification Search ............. 435/5, 6, 435/7.1, 7.2; 536/25.32, 26.6; 422/61
See application file for complete search history.

(56) References Cited

U.S. PATENT DOCUMENTS

2005/0203289 A1    9/2005    Schwartz et al.
2007/0004012 A1    1/2007    Sasikekharan et al.

OTHER PUBLICATIONS

Bioventures, Inc. et al., International Search Report and Written Opinion, PCT/US08/82091, Feb. 13, 2009.
Bioventures, Inc. et al., International Preliminary Report on Patentability, PCT/US08/82091, Feb. 18, 2010.

*Primary Examiner* — Jezia Riley
(74) *Attorney, Agent, or Firm* — David A. Farah; Sheldon Mak & Anderson

(57) ABSTRACT

A method for labeling biological molecules and synthetic molecules that contain a vicinal diol, such as RNA, carbohydrates or glycoproteins, using a periodate sequestering agent is provided. Compositions and kits for use in the labeling method are also provided.

23 Claims, 3 Drawing Sheets

METHOD, SUBSTANCES AND KITS FOR LABELING POPULATIONS OF RNA AND OTHER SUBSTANCES CONTAINING VICINAL DIOLS

CROSS REFERENCE TO RELATED APPLICATIONS

The present Application is a national stage of International Patent Application No. PCT/US2008/08291, titled "Method, Substances and Kits for Labeling Populations of RNA and Other Substances Containing Vicinal Diols," filed Oct. 31, 2008, which claims priority from U.S. Provisional Patent Application No. 60/984,308, titled "Method, Substances and Kits for Labeling Populations of RNA and Other Substances Containing Geminal Diols," filed Oct. 31, 2007, the contents of which are incorporated in this disclosure by reference in their entirety.

BACKGROUND

Frequently it is necessary to label molecules in order to provide a means of detecting and measuring the presence or absence of molecular entities, especially for the detection of biological molecules, chemical species and even certain types of organisms or cells. One of the trends to improve efficiency of identifying and quantifying these molecular or cellular entities is to perform multiplex types of analyses where the objective is to measure many of these species in a single assay such as microarrays or flow cytometric assays.

Presently, RNA species within a specimen are isolated and usually converted to their respective cDNAs for analysis by microarrays, quantitative real-time RT-PCR and other methods well known in the art. Many of these methods are time consuming, and suffer from sample losses during the various isolation and repeated purification steps required to be performed to obtain a result. In particular, many of the labeling agents presently used are very reactive and prone to decomposition especially in aqueous solutions and a substantial excess of labeling agents, relative to the species to be labeled, is frequently required for successful labeling. This is particularly the case for N-hydroxysuccinimide esters which are well known to be labile in aqueous media and have half-lives of only a few minutes. More importantly, these esters generally are used to modify primary amines. Consequently if target substances lack this functionality they must be modified to provide a free amine, thus adding additional steps to the labeling process and usually requiring additional steps of purification leading to loss of some sample. Likewise, maleimides also suffer the same disadvantages with respect to their reactions with sulfhydryl groups. For example, methods presently described in the art rely on sequential reaction of the RNA or vicinal diol containing species, such as polysaccharides or glycosylated proteins or peptides, with periodate, usually neutralization of the periodate with glycerol, followed by separation of the oxidized RNA or resulting dialdehyde species of interest from the periodate to prevent reaction of periodate with the labeling moiety by, for example, ethanol precipitation, exclusion chromatography and the like. The isolated oxidized RNA or dialdehyde reaction product is then reacted with a hydrazide containing signal moiety and a second physical separation of the labeled RNA or dialdehyde species is performed such as ethanol precipitation, or chromatography. Because periodate is usually employed in the periodate reaction of vicinal hydroxyl groups, the scavenging of periodate with glycerol is ineffective in removing the periodate, merely diverting the reaction to another species, yet introducing promiscuous dialdehydes to the reaction which can consume significant portions of the labeling agent with consequent diversion to unproductive labeling of irrelevant species, namely the dialdehydes arising from the oxidation of glycerol or other vicinal diol containing scavengers. There is a need for rapid labeling methods without these limitations.

SUMMARY

One embodiment of the present invention is a method for labeling a substance that contains vicinal diols, such as RNA, carbohydrates, glycosylated proteins and the like. According to the method, first, a vicinal diol containing substance is provided. Then, a periodate salt is added to the vicinal diol containing substance. The vicinal diol containing substance is capable of being oxidized with periodate to produce an aldehyde containing substance. An alkaline earth metal salt is then added, as well as a signal label, where the signal label is capable of reaction with the aldehyde containing substance, to produce a signal labeled substance. The method may further comprise separating the signal labeled substance, and/or analysis of the signal labeled substance.

In a preferred embodiment, the alkaline earth metal salt is a barium salt, more preferably, the alkaline earth metal salt is barium acetate, separately added, or generated in situ. In other preferred embodiments, the vicinal diol containing substance is one, or a combination of an RNA, a protein, a streptavidin and an avidin.

In another preferred embodiment of the method of the invention, the signal label is a hydrazide containing moiety comprising the nitrogen linkage —NH—NH$_2$, and the hydrazide containing moiety is attached to a suitable label. More preferably, the hydrazide containing signal moiety is selected from the group consisting of hydrazides, semicarbazides, carbohydrazides, and hydroxylamine derivatives, and the label of the signal label is selected from the group consisting of enzymes, fluorescent labels, chemiluminescent labels, electroluminescent labels, and biotin.

Another embodiment of the present invention is a composition for use in the labeling method of the invention. According one embodiment, the composition comprises an aqueous carrier and an alkaline earth metal salt, preferably, the alkaline earth metal salt is a barium salt. The composition may also comprise a signal label capable of reaction with an aldehyde containing substance, preferably a hydrazide containing moiety as described herein.

In another embodiment, a kit is provided with one or more reagents for use in the labeling method of the invention. According to one embodiment, the kit comprises one or more of the following reagents selected from the group consisting of a periodate salt, an alkaline earth metal salt, and a signal label capable of reaction with an aldehyde containing substance, wherein the reagents are in their elemental form or provided in an aqueous solution. The kit may also comprise one or more aqueous buffers. According to another embodiment, the kit for use in a method for labeling a substance that contains a vicinal diol comprises an alkaline earth metal salt and instructions for labeling a substance that contains a vicinal diol. The kit may also comprise a periodate salt, and/or a signal label capable of reaction with an aldehyde containing substance.

FIGURES

These and other features, aspects and advantages of the present invention will become better understood from the following description, appended claims, and accompanying figures where:

FIG. 1 is a graph showing the results of the labeling reaction of the RNA sequence, hsa-let-7e according to one embodiment of the present invention;

FIG. 2 is a graph showing the results of the labeling reaction of a yeast RNA according to another embodiment of the present invention;

FIG. 3 is a graph showing the labeling reaction components only, no microRNA, according to another embodiment of the present invention;

FIG. 4 is a graph showing the results of the labeling reaction of the RNA sequence, hsa-let-7a according to one embodiment of the present invention; and FIG. 5 is a graph showing the results of the labeling reaction of a yeast RNA sequence according to one embodiment of the present invention.

DESCRIPTION

According to one embodiment, the invention comprises a method for labeling a substance that contains vicinal diols. According to the method, we have found that periodate salts in conjunction with a periodate-sequestering-agent and fluorescent hydrazides and related compounds can label vicinal diol containing compounds, such as RNA, and glycosylated substances, such as proteins, rapidly and efficiently without degradation in a very rapid process. Separation of the vicinal diol containing compounds containing the hydrazide label requires only a brief centrifugal passage over a separation column.

The method and reagents disclosed herein are distinguished over methods presently described in the art. Such known methods rely on sequential reaction of the RNA or vicinal diol containing species with periodate, usually neutralization of the periodate with glycerol, which is then followed by separation of the oxidized RNA or resulting dialdehyde species of interest from the periodate to prevent reaction of periodate with the labeling moiety by, for example, ethanol precipitation, exclusion chromatography and the like. The isolated oxidized RNA or dialdehyde reaction product is then reacted with a hydrazide containing signal moiety and a second physical separation of the labeled RNA or dialdehyde species is performed such as ethanol precipitation, or chromatography. The scavenging of periodate with glycerol is ineffective in removing the periodate, merely diverting the reaction to another species yet introducing promiscuous dialdehydes to the reaction which can consume significant portions of the labeling agent and diverting the reaction products to unproductive labeling of irrelevant species, namely the dialdehydes arising from the oxidation of glycerol.

The simplicity and superiority of the method and substances described herein over the current art will be made clear by the following description and examples.

Referring now to Scheme I below, one embodiment of the invention, a method for labeling a vicinal diol containing substance is shown. As shown in Scheme I, first, a vicinal diol containing substance (1) capable of being oxidized with periodate is provided. Then, a periodate salt (2) is added to the vicinal diol containing substance (1), followed by the addition of a periodate sequestering agent ($M^+X^-$, 3), such as a barium salt. The reaction is allowed to proceed and the periodate salt (2) is allowed to cleave the vicinal diol containing substance into a resulting dialdehyde (4). Then, a signal label containing moiety, such as a signal molecule containing at least one functional group capable of reaction with aldehydes (N-label, 5) is then added to the dialdehyde (4). The resulting labeled substance (6) may then be separated and analyzed according to known methods.

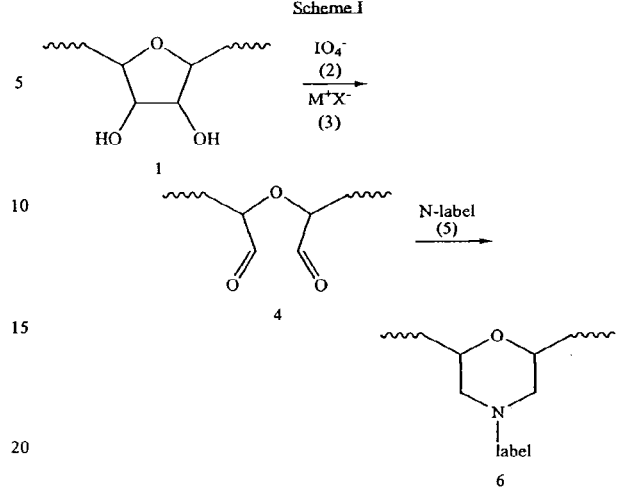

Scheme I

The alkaline earth metal salt (M+X−) is added to the reaction mixture in an amount such that the concentration of metal anions and the initial concentration of periodate ions are substantially equal. To assure complete sequestering of periodate ions and iodate ions arising from the oxidation of the diols, the metal ions are in slight excess of 2%-20%, preferably on the order of 5%-10% molar excess to periodate and iodate ions.

In a preferred embodiment the alkaline earth metal is barium, such as in barium salts including barium chloride and barium acetate. The alkaline earth metal salt may be mixed, such as by the addition of barium chloride and sodium acetate to the reaction, a mixed alkaline earth metal solution, and combinations thereof. Alternately, one alkaline earth metal salt may be used according to the invention. Preferably, the alkaline earth metal salt is soluble, or at least partially soluble in the reaction mixture.

The signal label containing moiety is a molecule containing at least one functional group capable of reaction with aldehydes (N-label, 5), as are known in the art, for example, primary amines, hydrazides, semihydrazides, carbohydrazides, thiocarbazides and hydroxylamines are examples of functional groups which can react with aldehydes. The term hydrazide, as used herein, describes hydrazide containing moieties, i.e., compounds containing the nitrogen linkage —NH—$NH_2$, such as hydrazides, semicarbazides and carbohydrazides, as well as hydroxylamine derivatives attached to suitable labels. Those skilled in the art will recognize that a variety of hydrazides are useful for the purposes set forth herein.

The signal component or "label" of the signal molecule may be at least one of the group consisting of enzymes, fluorescent labels, chemiluminescent labels, electroluminescent labels, and other labels known in the art, such as biotin.

According to one embodiment, the signal label is added to the alkaline earth metal treated reaction mixture without physical separation of the periodate from the oxidized nucleic acid or dialdehyde reaction product. For example, the signal label may be added directly to the alkaline earth metal treated reaction mixture, usually in the range of 0.5 μg-4 μg of labeling agent in a volume of 1-5 μl of suitable solvent, usually aqueous media. The labeling reaction is allowed to proceed for a period of one minute to one hour, more usually from 5 minutes to 15 minutes at ambient temperature. The reaction can be accelerated by the application of heat usually 37° C., but those skilled in the art will recognize that other temperatures or times can be utilized based on the nature and physical properties of the species being labeled and their compatibility with other times and temperatures.

According to another embodiment, the invention is a method for labeling RNA, as shown in Scheme II. The method comprises first, providing a sample of RNA (7), total or fractionated into subpopulations. The RNA (7) is treated with a periodate salt (8) in buffered aqueous media, followed by the addition of a soluble barium salt (9). The reaction is allowed to proceed to produce the resultant aldehyde (10). The hydrazide containing label (label-hydrazide, 11) is then allowed to react with the aldehyde (10). The reaction between the label-hydrazide (11) and the aldehyde (10) is allowed to proceed, producing labeled RNAs (12). The labeled RNAs (12) may be separated from the other reaction components by a brief centrifugation of the reaction mixture over a molecular size fractionation column. The labeled RNAs (12) obtained are suitable for use in microarrays, flow analysis and fluorescent capillary electrophoresis as well as other methods well known in the art.

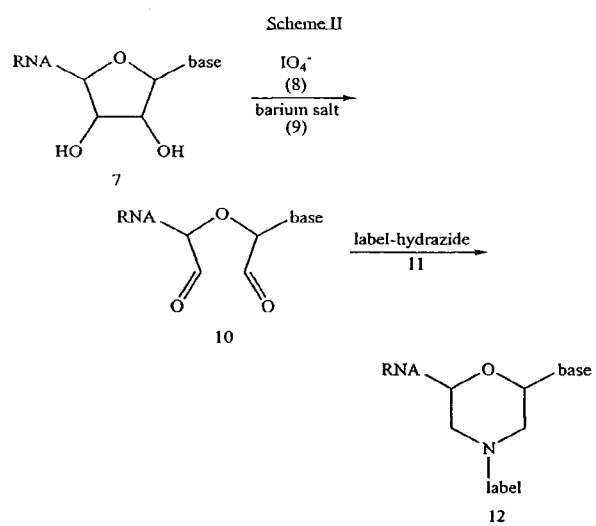

The RNA sample or other sample of vicinal diol containing substance used according to the invention may be obtained from a biological source such as microorganisms, plants and animals by methods well known in the art. For example, there are a number of kits designed to isolate total RNA or subfractions such as messenger RNAs, microRNAs and ribosomal RNAs which can be obtained from vendors such as Qiagen, Invitrogen and Ambion indicate but a few such suppliers. RNA suitable for the labeling method set forth should be in either water, deionized formamide or amine free buffers such as phosphate buffered saline, citrate, MES, MOPS, HEPES, acetate and the like usually at neutral pH or alternatively the RNA can be in a dry or lyophilized from provide that there are no free primary amines present.

The RNA solution may be used in a small volume such as 0.5 µl-10 µl and usually in the quantity of 0.5-10 µg of RNA. Dry RNA may be brought into solution with water or the reaction buffer described below. The RNA to be labeled is then brought into contact with a solution of a periodate salt, usually sodium or potassium salt at a concentration of between 1 mM and 100 mM such that the final periodate concentration is between 0.1 and 10 mM in the combined solutions of RNA and periodate. The periodate salt may be dissolved in water. The reaction is buffered to a pH of 4.0-8.0, preferably between pH 4.5 and 7.2. For example MES buffer pH 4.7 in the range of 0.1 M-0.01 M is added. Likewise acetate buffers over similar concentration and pH ranges can be utilized. The reaction is then incubated at a temperature between 20° C. and 50° C., usually for convenience at ambient temperatures near ~25° C. The time of incubation is from 5 minutes to 1 hour usually between 15 minutes and 30 minutes, preferably protected from light. Following incubation an amount of an aqueous solution of an alkaline earth metal salt, such as barium chloride or barium acetate is added to the reaction mixture, such that the concentration of barium ions and the initial concentration of periodate ions are substantially equal. To assure complete sequestering of periodate ions and iodate ions arising from the oxidation of the diols, barium is in slight excess of 2%-20%, preferably on the order of 5%-10% molar excess to periodate and iodate ions. Preferably, the barium salt is barium acetate.

The label-hydrazide may be added to the reaction mixture without isolation of the aldehyde reaction product. For example, fluorescein hydrazide may be added to the barium treated reaction mixture without physical separation of the periodate from the oxidized nucleic acid or dialdehyde reaction product. More specifically, fluorescein carbohydrazide may be added directly to the barium treated reaction mixture, usually in the range of 0.5 µg-4 µg of labeling agent in a volume of 1-5 µl of suitable solvent, usually aqueous media. The labeling reaction is allowed to proceed for a period of one minute to one hour, more usually from 5 minutes to 15 minutes at ambient temperature, or may be accelerated by the application of heat, usually 37° C. However, those skilled in the art will recognize that other temperatures or times can be utilized based on the nature and physical properties of the species being labeled and their compatibility with other times and temperatures.

According to another embodiment, the invention comprises a composition for use according to the method described herein. In one embodiment the composition comprises a periodate salt and a buffered aqueous media. In another embodiment, the composition comprises an alkaline earth metal salt and a signal label. Preferably, the soluble alkaline earth metal salt is a barium salt.

According to another embodiment, the invention comprises a kit for use in the method described herein. The kit comprises one or more than reagent for use the in the method of the invention. Preferably the kit comprises one or more of the following reagents selected from a periodate salt, a buffered aqueous media, an alkaline earth metal salt, and a signal label. Preferably, the alkaline earth metal salt is soluble, or solubilized in the reaction mixture, and preferably, the alkaline earth metal salt is a barium salt, more preferably barium acetate. Preferably, the signal label is a hydrazide containing signal label, capable of reaction with an aldehyde.

The compositions, methods and systems described herein may include other materials and/or modifications as necessary as will be understood by those of skill in the art by reference to this disclosure and the invention is understood not to be limited by the foregoing examples.

EXAMPLES

Example 1

Hydrazide Labeling of RNA Using Periodiate Oxidation

Synthetic miRNA

The synthetic miRNA(syn-miRNA) were selected and designed to specifically reflect a set of human miRNAs. The syn-miRNA were obtained from Integrated DNA Technologies (Coralville, Iowa). Each syn-miRNA was resuspended a stabilization buffer containing 1 mM Sodium Citrate (Ambion; Austin, Tex.) and 30% deionized formamide (Bioventures; Murfreesboro, Tenn.) to a final concentration of 100 pmol/µl. The syn-miRNA's were then aliquoted into 10 µl working stocks in 0.5 ml tubes (Nalgene; Rochester, N.Y.). The names and sequences of the RNA sequences used in the following examples are shown below in Table 1.

TABLE 1

| NAME | SEQUENCE | SEQ ID NO: |
|---|---|---|
| hsa-let-7a | /5Phos/rUrGrArGrGrUrArGrUrArGrGrUrUrGrUrArUrArGrUrU | SEQ ID NO: 1 |
| hsa-let-7e | /5Phos/rUrGrArGrGrUrArGrGrArGrGrUrUrGrUrArUrArGrU | SEQ ID NO: 2 |
| hsa-miR-106a | /5Phos/rArArArArGrUrGrCrUrUrArCrArGrUrGrCrArGrGrUrArGrC | SEQ ID NO: 3 |
| hsa-miR-126* | /5Phos/rCrArUrUrArUrUrArCrUrUrUrGrGrUrArCrGrCrG | SEQ ID NO: 4 |
| hsa-miR-135a | /5Phos/rUrArUrGrGrCrUrUrUrUrUrArUrUrCrCrUrArUrGrUrGrA | SEQ ID NO: 5 |
| hsa-miR-138 | /5Phos/rArGrCrUrGrGrUrGrUrUrGrUrGrArArUrC | SEQ ID NO: 6 |
| hsa-miR-154 | /5Phos/rUrArGrGrUrUrArUrCrCrGrUrGrUrUrGrCrCrUrUrCrG | SEQ ID NO: 7 |
| hsa-miR-154* | /5Phos/rArArUrCrArUrArCrArCrGrGrUrUrGrArCrCrUrArUrU | SEQ ID NO: 8 |

Yeast tRNA

Purified Yeast tRNA was obtained from Ambion; Austin, Tex.).

Periodate Oxidation and Hydrazide Labeling

Oxidation was carried out by adding an oxidation mix to each well of a Bio-Rad 96-well Multiplate consisting of 100 mM Sodium Periodate (Sigma Chemical Co; St. Louis, Mo.) and 100 mM MES(2-(N-morpholino)ethanesulfonic acid), pH 4.7 (Sigma Chemical Co), to 20 pmol of hsa-miR-7e in well A1 of a Bio-Rad 96-well Multiplate, 2 µg of yeast tRNA in well B1 and in C1 no RNA for a final volume of 9 µl.

The plate was then briefly pulsed in a centrifuge to mix components and placed in the dark at room temperature for 30 minutes. After 30 minutes 0.55 µl of 100 mM Barium Chloride (Sigma Chemical Co.) was added to each well followed by adding 0.45 µl of 10 µg/µl FAM-5-thiosemicarbozide (Anaspec, Inc.; San Jose, Calif.). The plate was then briefly pulsed in a centrifuge to mix components and placed in the dark at room temperature for 15 minutes.

Labeling Reaction Clean-Up

After 15 minutes of the labeling of the RNAs, Micro Select-D, G25 TE (IBI-Shelton SCIENTIFIC; Peosta, Iowa) were used to remove the unreacted dye. The Micro Select-D columns were each placed in a 2 ml collection tube (IBI-Shelton SCIENTIFIC). The column/collection tubes were placed in a microcentrifuge, IEC MicromaxRX (Thermo Scientific; Waltham, Mass.) and spun at 1,000×g for 2 minutes to remove the hydrating fluid. The columns were then placed into new 2 ml collection tubes and the reaction mixture was loaded onto each column, being careful not to disturb the column resin. After 3 minutes the column/collection tubes were placed in the microcentrifuge (Thermo Scientific) and spun at 1,000×g for 5 minutes to collect the purified labeled RNA.

An additional cleanup to remove any unreacted dye was carried out by ethanol precipitation. 2 µl of 3M Sodium Acetate, 300 µl of 100% Ethanol and 1 µl of glycogen was added to each reaction tube then placed at −80° C. overnight. Tubes were spun at 12,000×g for 30 minutes at 4° C. to pellet the RNA, the ethanol was then drawn off and discarded. The pellet was washed with 200 µl of 95% ethanol, vortexed briefly then spun tubes at 12,000×g for 30 minutes at 4° C. to pellet the RNA, and the ethanol drawn off and the ethanol wash was repeated one additional time. After drawing off the ethanol from the last wash the tubes were placed in a Speed-Vac (Sorvall) at low temperature for 10 minutes to evaporate any remaining ethanol. After the samples were dried, 20 µl of sterile water was added to resuspend the recovered labeled samples (RNAs).

Analysis of the microRNA Labeling

1 µl of the cleaned labeled product was added to a 96-well Multiplate (Bio-Rad) containing 18.5 µl DI Formamide (Bio Ventures, Inc., Murfreesboro, Tenn.) and 0.5 µl of 20 fmol each of Hex labeled oligonucleotides (BioVentures, Inc., Murfreesboro, Tenn.) ranging in size from 15 bp, 20 bp, 25 bp, 30 bp, 35 bp, 40 bp, 45 bp, 50 bp. The plate was then briefly pulsed in a centrifuge, Allegra 31 (Beckman Coulter; Fullerton, Calif.) to mix components then placed on an ABI Prism® 3100 DNA Analyzer (Applied Biosystems; Foster City, Calif.) and were analyzed using the Genescan program, Dye Set "D," module file "GeneScan_030507_microshort," with an injection voltage of 1 kvolt, injection time of 22 seconds and a run times of 1,000 seconds. The raw data was analyzed using GeneScan software (Applied Biosystems).

Referring now to FIG. 1, a plot of the results of the labeling reaction of the RNA sequence, hsa-let-7e, a sequence of 24 bp in length, is shown. Referring now to FIG. 2, a plot of the results of the labeling reaction of yeast tRNA, of a sequence approximately 80 bp in length, is shown. Referring now to FIG. 3, a plot of the results of the labeling reaction components only, no microRNA, is shown. The results of the electrophoretic analysis of the labeled reaction products, as shown in FIGS. 1-3, indicated that the chemical labeling was completed and the products migrated at their expected fragment size, while there was no evidence of any labeling when RNA was not present.

Example 2

Hydrazide Labeling of RNA Using Periodate Oxidation (Acetate Method)

Synthetic miRNA

The synthetic RNAs and yeast tRNAs as used in example one were utilized as follows.
Periodate Oxidation and Hydrazide Labeling Oxidation was carried out by adding periodate buffer [(1 mM final reaction concentration Sodium Periodate (Sigma Chemical Co; St. Louis, Mo.) and 1 mM final reaction concentration Sodium Acetate, pH 5.7 (Sigma Chemical Co)], to either 20 pmol of hsa-miR-7a or 2 ug of yeast tRNA in a Bio-Rad 96-well Multiplate to a final volume of 9 ul. The plate was then briefly pulsed in a centrifuge to mix components and placed in the dark at room temperature for 30 minutes. After 30 minutes 0.55 µl of 10 mM Barium Chloride, brought into solution in 100 mM Sodium Acetate (Sigma Chemical Co.) was added to each reaction well. Following the barium addition, 0.45 µl of 1 µg/µl FAM-5-thiosemicarbozide (Anaspec, Inc.; San Jose, Calif.) brought up in Dimethylformamide (Sigma Chemical Corp., Saint Louis, Mo.) was added to each reaction well. The plate was then briefly pulsed in a centrifuge to mix components and placed in the dark at room temperature for 15 minutes.
Labeling Reaction Clean-Up After labeling the RNAs, Micro spin columns (Thermo Scientific; Pittsburgh, Pa.), packed with 0.06 g Sephadex G25 and hydrated with 300 µl 1X Tris-EDTA, were used to remove the uncoupled dye. The Micro spin columns were each placed in a 1.5 ml collection tube (USA/Scientific; Ocela, Fla.). The column/collection tubes were placed in a microcentrifuge, IEC MicromaxRX (Thermo Scientific; Waltham, Mass.) and spun at 1,200×g for 5 minutes to remove the hydrating fluid. The columns were then placed into new 1.5 ml collection tubes and the sample was loaded onto each column being careful not to disturb the column resin. After 3 minutes, the column/collection tubes were placed in the microcentrifuge and spun at 1,200×g for 5 minutes to collect the purified labeled RNA samples.
Analysis of the microRNA Labeling 1 µl of the cleaned labeled product was added to a new 96-well Multiplate (Bio-Rad) containing 18.5 µl DI Formamide (Bio Ventures Inc., Murfreesboro, Tenn.) and 0.5 µl of 20 fmol each of Hex labeled oligonucleotides (BioVentures, Inc.) ranging in size from 15 bp, 20 bp, 25 bp, 30 bp, 35 bp, 40 bp, 45 bp, 50 bp. The plate was then briefly pulsed in a centrifuge, Allegra 31 (Beckman Coulter; Fullerton, Calif.) to mix components then placed on an ABI Prism® 3100 DNA Analyzer (Applied Biosystems; Foster City, Calif.) and were analyzed using the Genescan program, Dye Set "D," module file "GeneScan_030507_microshort," with an injection voltage of 1 kvolt, injection time of 22 seconds and a run times of 1,000 seconds. The raw data was analyzed using GeneScan software (Applied Biosystems).

Referring now to FIG. 4, a plot of the results of the labeling reaction of the RNA sequence hsa-let-7a, an RNA sequence of 24 bp in length, is shown. Referring now to FIG. 5, a plot of the results of the labeling reaction of yeast tRNA, an RNA sequence of approximatly 80 bp (multiplet) in length, is shown. The results of the electrophoretic analysis of the labeled reaction products, as shown in FIGS. 4 and 5, demonstrated that the chemical labeling was completed and the products migrated at their expected fragment size while there was no evidence of any labeling when RNA was not present.

Example 3

Hydrazide Labeling of Streptavidin/Avidin Using Periodate Oxidation

Preparation of Streptavidin and Avidin

Streptavidin (Roche Applied Science; Indianapolis, Ind.) was brought into solution in 0.5% Sodium Azide to a final concentration of 1 mg/mi and Avidin (Sigma Chemical Co; St. Louis, Mo.) was brought into solution in 0.5% Sodium Azide for a final concentration of 1 mg/ml.
Periodate Oxidation and Hydrazide Labeling Oxidation of Streptavidin and avidin prepared above was carried out by adding periodate buffer [(1 mM final reaction concentration Sodium Periodate (Sigma Chemical Co; St. Louis, Mo.) and 1 mM final reaction concentration Sodium Acetate, pH 5.7 (Sigma Chemical Co)], to each of 1 µl of Streptavidin, 1 µl of Avidin, or 1 µl of sterile water in a Bio-Rad 96-well Multiplate to a final volume of 9 µl.

The plate was then briefly pulsed in a centrifuge to mix components and placed in the dark at room temperature for 30 minutes. After 30 minutes, 0.55 µl of 10 mM Barium Chloride, brought into solution in 100 mM Sodium Acetate (Sigma Chemical Co.), was added to each reaction well. Following the barium addition, 0.45 µl of 1 µg/µl FAM-5-thiosemicarbozide (Anaspec, Inc.; San Jose, Calif.), brought up in Dimethylformamide (Sigma Chemical Corp.), was added to each reaction well. The plate was then briefly pulsed in a centrifuge to mix components and placed in the dark at room temperature for 15 minutes.
Labeling Reaction Clean-up After labeling the samples, Micro spin columns (Thermo Scientific; Pittsburgh, Pa.) packed with 0.06 g Sephadex G25 and hydrated with 300 µl 1X Tris-EDTA were used to remove the uncoupled dye. The Micro spin columns were each placed in a 1.5 ml collection tube (USA/Scientific; Ocela, Fla.). The column/collection tubes were placed in a microcentrifuge, IEC MicromaxRX (Thermo Scientific; Waltham, Mass.) and spun at 1,200×g for 5 minutes to remove the hydrating fluid. The columns were then placed into new 1.5 ml collection tubes and the sample was loaded onto each column being careful not to disturb the column resin. After 3 minutes, the column/collection tubes were placed in the microcentrifuge and spun at 1,200×g for 5 minutes to collect the purified labeled samples.
Analysis of the microRNA labeling The labeled reactions were analyzed by reading the fluorescence on a Nanodrop 3300 Fluorospectrometer (Nanodrop Technologies; Wilmington, Del.), measured using 470 nm excitation source, with the emission wavelength monitored at 515 nm. The results were as follows:

Streptavidin labeling reaction gave a reading of 413.4 RFU's equivalent to 87.2 fmols Avidin labeling reaction gave a reading of 592.1 RFU's equivalent to 111.36 fmols No target control labeling reaction gave a reading of 51.2 RFU's equivalent to 17.7 fmols The labeled streptavidin was 5 times the amount of uncoupled dye and the avidin was 6 times the amount of uncoupled dye indicating that the proteins had been labeled by the dye.

Although the present invention has been discussed in considerable detail with reference to certain preferred embodiments, other embodiments are possible. Therefore, the scope of the appended claims should not be limited to the description of preferred embodiments contained herein.

SEQUENCE LISTING

<160> NUMBER OF SEQ ID NOS: 7

<210> SEQ ID NO 1
<211> LENGTH: 22
<212> TYPE: RNA
<213> ORGANISM: Artificial
<220> FEATURE:
<223> OTHER INFORMATION: Synthetic

<400> SEQUENCE: 1
ugagguagua gguuguauag uu                                             22

<210> SEQ ID NO 2
<211> LENGTH: 21
<212> TYPE: RNA
<213> ORGANISM: Artificial
<220> FEATURE:
<223> OTHER INFORMATION: Synthetic

<400> SEQUENCE: 2
ugagguagga gguuguauag u                                              21

<210> SEQ ID NO 3
<211> LENGTH: 24
<212> TYPE: RNA
<213> ORGANISM: Artificial
<220> FEATURE:
<223> OTHER INFORMATION: Synthetic

<400> SEQUENCE: 3
aaaagugcuu acagugcagg uagc                                           24

<210> SEQ ID NO 4
<211> LENGTH: 21
<212> TYPE: RNA
<213> ORGANISM: Artificial
<220> FEATURE:
<223> OTHER INFORMATION: Synthetic

<400> SEQUENCE: 4
cauuauuacu uuugguacgc g                                              21

<210> SEQ ID NO 5
<211> LENGTH: 23
<212> TYPE: RNA
<213> ORGANISM: Artificial
<220> FEATURE:
<223> OTHER INFORMATION: Synthetic

<400> SEQUENCE: 5
uauggcuuuu uauuccuaug uga                                            23

<210> SEQ ID NO 6
<211> LENGTH: 17
<212> TYPE: RNA
<213> ORGANISM: Artificial
<220> FEATURE:
<223> OTHER INFORMATION: Synthetic

<400> SEQUENCE: 6
agcugguguu gugaauc                                                   17

<210> SEQ ID NO 7
<211> LENGTH: 22
<212> TYPE: RNA

```
<213> ORGANISM: Artificial
<220> FEATURE:
<223> OTHER INFORMATION: Synthetic

<400> SEQUENCE: 7
uagguuaucc guguugccuu cg                                           22
```

What is claimed is:

1. A method for labeling a substance that contains a vicinal diol, the method comprising:
   (a) providing a vicinal diol containing substance;
   (b) adding a periodate salt to the vicinal diol containing substance to form a reaction mixture, wherein the vicinal diol containing substance is capable of being oxidized with periodate to produce an aldehyde containing substance;
   (c) adding an alkaline earth metal salt to form an alkaline earth metal treated reaction mixture; and
   (d) adding a signal label to the alkaline earth metal treated reaction mixture, the signal label being capable of reaction with the aldehyde containing substance, to produce a signal labeled substance.

2. The method of claim 1, wherein the method further comprises separating the signal labeled substance.

3. The method of claim 1, wherein the method further comprises analysis of the signal labeled substance.

4. The method of claim 1, wherein the alkaline earth metal salt is a barium salt.

5. The method of claim 1, wherein the alkaline earth metal salt is barium acetate.

6. The method of claim 1, wherein the vicinal diol containing substance is RNA.

7. The method of claim 1, wherein the vicinal diol containing substance is a protein.

8. The method of claim 1, wherein the vicinal diol containing substance is a streptavidin.

9. The method of claim 1, wherein the vicinal diol containing substance is an avidin.

10. The method of claim 1, wherein the signal label is a hydrazide containing moiety comprising the nitrogen linkage —NH—NH$_2$, and wherein the hydrazide containing moiety is attached to a suitable label.

11. The method of claim 10, wherein the hydrazide containing signal moiety is selected from the group consisting of hydrazides, semicarbazides, carbohydrazides, and hydroxylamine derivatives.

12. The method of claim 1, wherein the label of the signal label is selected from the group consisting of enzymes, fluorescent labels, chemiluminescent labels, electroluminescent labels, and biotin.

13. The method of claim 12, wherein the label is a fluorescent label.

14. The method of claim 12, wherein the label is biotin.

15. The method of claim 1, wherein:
   (a) the vicinal diol containing substance is a vicinal diol containing RNA;
   (b) the periodate salt is added to the vicinal diol containing RNA to form a reaction mixture, wherein the vicinal diol containing RNA is capable of being oxidized with periodate to produce an aldehyde containing RNA derivative;
   (c) the alkaline earth metal salt is added to the reaction mixture to form an alkaline earth metal treated reaction mixture; and
   (d) the signal label is capable of reaction with the aldehyde containing RNA, to produce a signal labeled RNA derivative.

16. The method of claim 15, wherein the alkaline earth metal salt is a barium salt.

17. A composition for use in the method of claim 1, the composition comprising:
   an aqueous carrier;
   a periodate salt; and
   an alkaline earth metal salt.

18. The composition of claim 17, wherein the alkaline earth metal salt is a barium salt.

19. The composition of claim 17, the composition further comprising a signal label capable of reaction with an aldehyde containing substance.

20. The composition of claim 19, wherein the signal label is a hydrazide containing moiety comprising the nitrogen linkage —NH—NH$_2$, and wherein the hydrazide containing moiety is attached to a suitable label.

21. A kit comprising reagents for use in the method of claim 1, wherein the reagents comprise an alkaline earth metal salt; and further comprise one or more of the following reagents selected from the group consisting of a periodate salt, and a signal label capable of reaction with an aldehyde containing substance, wherein the reagents are in their elemental form or provided in an aqueous solution.

22. The kit of claim 21, further comprising one or more aqueous buffers.

23. The kit of claim 21, the kit further comprising:
   instructions for labeling a substance that contains a vicinal diol.

* * * * *